United States Patent [19]
Reedy

[11] 3,946,057
[45] Mar. 23, 1976

[54] PREPARATION OF METAL COMPLEXES OF 1,3-DIKETONES

[75] Inventor: James Dale Reedy, Williamstown, W. Va.

[73] Assignee: Union Carbide Corporation, New York, N.Y.

[22] Filed: Feb. 7, 1974

[21] Appl. No.: 440,514

Related U.S. Application Data

[63] Continuation-in-part of Ser. No. 250,046, May 3, 1972, abandoned.

[52] U.S. Cl. ....... 260/439 R; 260/429 J; 260/429.1; 260/429.2; 260/429.3; 260/429.9; 260/431; 260/438.1
[51] Int. Cl.² ................ C07C 49/12; C07C 49/14; C07C 49/16
[58] Field of Search ........ 260/429 R, 429 J, 439 R, 260/438.1, 429.9, 429.1, 429.2, 429.3, 431

[56] References Cited
UNITED STATES PATENTS

| | | | |
|---|---|---|---|
| 1,944,274 | 1/1934 | Salzberg | 260/429 R |
| 2,700,048 | 1/1955 | Schmidt | 260/439 R |
| 2,706,181 | 4/1955 | Pruitt et al. | 260/439 R |

OTHER PUBLICATIONS

Fernelius et al., Inorganic Syntheses, Vol. V, McGraw Hill Co., N.Y., N.Y.; 1957, pp. 105–109.

Dwyer et al., Chelating Agents and Metal Chelates; Academic Press, N.Y., N.Y.; 1964 p. 100.

*Primary Examiner*—Arthur P. Demers
*Attorney, Agent, or Firm*—Reynold J. Finnegan

[57] ABSTRACT

Process for preparing metal complexes of organic 1,3-diketones, which comprises, reacting in the presence of an alkylene oxide, a metal halide or hydrates thereof, and an organic 1,3-diketone.

12 Claims, No Drawings

PREPARATION OF METAL COMPLEXES OF 1,3-DIKETONES

This is a continuation-in-part of U.S. application, Ser. No. 250,046, filed May 3, 1972, now abandoned

BACKGROUND OF THE INVENTION

This invention relates to the production of metal complexes of 1,3-diketones. More particularly this invention relates to a process of preparing metal complexes of 1,3-diketones comprising reacting a metal halide or hydrates thereof, and an organic 1,3-diketone compound in the presence of an alkylene oxide.

Metal complexes or derivatives of organic 1,3-diketones, often referred to as metal chelates are well known in the art as witnessed for example by U.S. Pat. Nos. 3,231,597 and 3,291,660.

SUMMARY OF THE INVENTION

It has now been discovered that metal complexes of organic 1,3-diketones can be produced by reacting a metal halide or hydrates thereof and an organic 1,3-diketone in the presence of an alkylene oxide.

Therefore it is an object of this invention to provide an efficient and economical process for preparing metal complexes of organic 1,3-diketones. Other objects and advantages will become readily apparent from the following description and appended claims.

More specifically the instant invention may be described as a method for preparing metal complexes of organic 1,3-diketones which can be represented as having the general formula

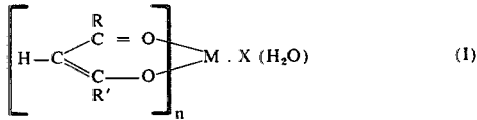 (I)

wherein R and R' are monovalent organic radicals, M is a metal cation, $n$ is an integer which corresponds to the electrovalence of M, and $x$ has a value of O or a positive integer, which method comprises reacting, in the presence of an alkylene oxide, a metal halide having the formula $M(X)_n \cdot y(H_2O)$ where M and $n$ are the same as defined above, X is halogen, and $y$ has a value of O or a positive integer, and an organic 1,3-diketone having the formula $RCOCH_2COR'$ wherein R and R' are the same as defined above.

DESCRIPTION OF THE PREFERRED EMBODIMENTS

The 1,3-diketones useful in the practice of this invention are those having the formula

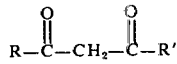

wherein R and R' are monovalent organic radicals which may be the same or different. Typical of such radicals are alkyl groups, such as methyl, ethyl, propyl, isopropyl, butyl, decyl, dodecyl, and the like; aryl groups, such as phenyl, napthyl, and the like; aralkyl groups, such as benzyl, phenylethyl, and the like; alkaryl groups, such as tolyl, dimethylphenyl, and the like; cycloalkyl groups, such as cyclopentyl, cyclohexyl, and the like; alkoxy groups, such as methoxy, ethoxy, and the like; haloalkyl groups, such as chloromethyl, chloropropyl, trifluoromethyl and the like; and haloaryl groups, such as chlorophenyl, bromophenyl, and the like. Preferably R and R' contain from 1 to 12 carbon atoms. Most preferably R and R' are methyl radicals. Illustrative examples of said 1,3-diketones are acetylacetone, benzoylacetone, 4,4,4-trifluoro-1-phenyl-1,3-butanedione; chlorobenzoylacetone, butanoylacetone, dibenzoylmethane, ethylacetoacetone, and the like.

The metal halides which are employable in the process of this invention are those of the formula $M(X)n \cdot y(H_2O)$ wherein M is a metal cation, n an integer which corresponds to the electrovalence of M, X is halogen, and y has a value of O or a positive integer. Illustrative examples of such metals include copper, zinc, mercury, indium, lanthanum, cerium, praseodymium, neodymium, samarium, zirconium, chromium, neodymium, uranium, manganese, iron, cobalt, nickel, platinum, palladium, cadmium, scandium, thorium, vanadium, gallium, thallium, ytturium, eruopium, gadolinium, hafnium, lead and plutonium, while the halogen ion of course can be chlorine, bromine, iodine, and the like. Alkali metal halides have not been found suitable for use in the process of the instant invention.

Thus it is obvious that the product metal complexes of this invention are anhydrous compounds when $x$ has a value of O and hydrated compounds when $x$ is a positive integer, e.g. from 1 to 6. Likewise the metal halide starting materials are anhydrous when $y$ has a value of O and hydrated when $y$ is a positive integer, e.g. from 1 to 8. Of course it is obvious that $x$ and $y$ may be the same or different. Alternatively, the compounds of formula (I) above may also be represented by the general formula

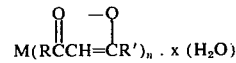

wherein M, R, R', $n$ and $x$ are the same as defined above.

Preferably said metal halides are chlorides, especially nickel chloride and/or hydrated nickel chloride. Illustrative examples of such metal halides are $NiCl_2$, $NiCl_2 \cdot 6H_2O$, $FeCl_3$, $FeCl_2$, $CuCl_2$, chromium chloride, vanadyl chloride, cerrous chloride, zirconium chloride, thorium chloride, and the like.

The alkylene oxides employable in the process of this invention are those containing from 2 to 8 carbon atoms. Illustrative examples of such epoxides are ethylene oxide, 1,2-propylene oxide, 1,3-propylene oxide, 1,2-butylene oxide, phenylethyl oxide, epoxyoctane, and the like. Preferably said epoxides are lower alkylene oxides containing from 2 to 4 carbon atoms, the most preferred being 1,2-propylene oxide.

The process of the instant invention is preferably conducted in the presence of an inert organic polar solvent. It is generally desired that the solvent be capable of dissolving both the organic and inorganic reactants so that the reaction medium is homogeneous. When the reaction medium is homogeneous very rapid reaction times, normally only a few minutes, have been obtained. In the event that the process should be practiced using an insoluble metal halide, reaction times would have to be increased accordingly and a higher reaction temperature and/or pressure would appear to be advantageous. The amount of solvent employed of course is not critical but is preferred to be at least that amount which will provide for a homogeneous reaction. The preferred inert organic polar solvents are lower alcohols, especially methanol. Water may be used but is generally not desired, since reaction rates are much slower than those conducted in methanol and the quality of the product diminished.

The reaction can be conducted over a wide range of temperatures and pressures. The pressure can be sub-atmospheric to super-atmospheric. Since reaction rates are quite fast the primary advantage in using super-atmospheric pressures is to suppress the loss of reactants, in particular, the alkylene oxide. For convenience the reaction is conducted at atmospheric pressure. The reaction temperature is influenced by the volatility of the alkylene oxide and pressure. In most instances the initial reaction is very fast at ambient temperature. Since the reaction process is exothermic, it is desirable not to allow the reaction medium to reach a temperature which would cause excessive loss of reactants by evaporation. For convenience most reactions are initiated at ambient temperatures and the rate of addition of alkylene oxide is limited to prevent loss by boiling of the reactants. It is generally preferred to maintain the reaction at temperatures of about 50°C. or below, i.e. from about 25°C. to about 50°C., which may be done by adding the alkylene oxide incrementally or by cooling the reaction chamber, e.g. with ice water.

The process of the instant invention is unique since in the absence of an alkylene oxide the extent of interaction between the metal halide and 1,3-diketone starting material may be so slight that no physical evidence of reaction is apparent. Upon addition of the alkylene oxide the complex formation of the metal derivative of organic 1,3-diketone is generally completed within a matter of minutes. This general reaction may be described by the following illustrative equation

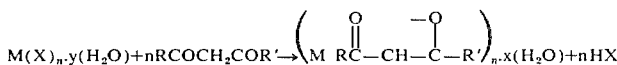

$$M(X)_n \cdot y(H_2O) + nRCOCH_2COR' \rightarrow \left( M \underset{RC-CH-C-R'}{\overset{O\ \ \ -O}{\parallel\ \ \ \parallel}} \right)_n \cdot x(H_2O) + nHX$$

wherein M, X, R, R', n, x and y, are the same as defined above. The hydrogen halide is formally eliminated and scavenged by the alkylene oxide during the process to produce halohydrin by-products which can be removed by any suitable method such as distillation, solvent extraction, and the like. Certain chlorohydrins may not be sufficiently stable to allow themselves to be distilled from the metal complex product. If desired, the hydrated metal complexes can be dehydrated by any suitable method, for example by azeotropic distillation of an aqueous solvent solution of hydrated metal complex which removes the water and renders the anhydrous metal complex soluble in the solvent. Any suitable inert organic solvent may be employed, such as xylene and the like.

The reaction stoichiometry is obviously not narrowly critical, the amounts of reactants employed merely depending upon the particular metal complex product to be produced, the reaction conditions employed and the reaction efficiency desired. Obviously the amount of organic 1,3-diketone starting material employed need only be sufficient to produce that amount of metal complex product desired. However, in order to insure efficient utilization of the metal an amount of 1,3-diketone starting material in excess (e.g., 1–20 per cent) of the amount stoichiometrically necessary to convert all of the metal halide to the desired metal complex product is preferred and recommended. Likewise the amount of alkylene oxide employed is governed in part by the amount of hydrogen halide to be eliminated. Again for efficient results it is preferred and recommended to employ an amount of alkylene oxide in excess (e.g., 1–20%) of the amount stoichiometrically necessary to eliminate all of the hydrogen halide by-products that may be formed by the process. Of course it is also understood that a finite amount of interaction between the metal halide and 1,3-diketone is necessary for the alkylene oxide to function. However, with certain metal halides which can react directly with alkylene oxide the interaction between the metal halide and 1,3-diketone may not be necessary. In this case alkoxides are formed as intermediates and these in turn react with the ketone.

The process of the instant invention possesses many unique features. For example, it provides for the rapid production of metal complexes of organic 1,3-diketones which products are insoluble in the reaction medium in which they are prepared. The reaction is usually complete within a matter of a few minutes at temperatures below 50°C. This is in contrast to prior art reactions employing metal oxides, hydroxides or carbonates which may require several hours to go to completion. Moreover in the instant process the reaction temperature can be controlled by the rate of alkylene oxide addition, there are no disadvantageous side reactions and the use of buffers which introduce extraneous impurities into the product are unnecessary. The metal complex products of the instant process are obtained in high yields and high purity and do not have to be recrystallized unless desired. The by-products of the instant invention are easily removed by conventional methods. The process of the instant invention is especially suitable for producing metal complexes of 1,3-diketones on a commercial scale.

The metal complex organic 1,3-diketone products of the instant invention have a wide range of utility well known in the art. For example, they can be employed as metal chelate catalysts in the preparation of polyurethane formulations, as witnessed by U.S. Pat. Nos. 3,231,597 and 3,291,660. They can also be used as catalysts in the production of mechanically frothed polyurethane foam as described in U.S. Pat. No. 3,772,224. In general they are a unique source for introducing metals into the preparation of organometallics, a source of metal or oxides for controlled deposition, fungicides, pigments, color stabilizers, carbon scavengers for disel fuels, bonding agents for plastic to metal seals and as combustion control catalysts for rocket fuels.

The following examples are illustrative of the present invention and are not to be regarded as limitative. It is to be understood that all parts, percentages and proportions referred to herein and in the appended claims are by weight unless otherwise indicated.

EXAMPLE 1

Preparation of nickel (II) acetylacetonate dihydrate.

To a flask containing a solution composed of 17.7 grams (0.0745 moles) of hydrated nickel chloride (NiCl$_2$.6H$_2$O), 30 ml. of methanol and 18 grams (0.18 moles) of acetylacetone (2,4-pentanedione) was added incrementally 17.4 grams (0.30 moles) of 1,2-propylene oxide at ambient temperature and atmospheric pressure. The addition rate of propylene oxide was such that the heat of reaction was maintained at a temperature of about 50°C. The total addition time was less than 15 minutes. Within about 5 minutes after the final addition of propylene oxide, blue nickel (II) acetylacetonate dihydrate crystals formed very rapidly and occupied essentially all of the volume formerly taken by the original solution. The crystal metal complex product was transferred to a filter and washed with 50 ml. of hexane and then 60 ml. of methanol ro remove the chlorohydrin by-product and any residual nickel chloride. The metal complex product was air dried and then analyzed. The overall yield of pure nickel acetylacetonate dihydrate was about 85 per cent.

| Product Analysis: | %Ni | %C | %H |
|---|---|---|---|
| Calcd.: | 20.0 | 41.0 | 6.15 |
| Found: | 19.8 | 41.7 | 6.3 |

The dehydrated nickel acetylacetonate metal complex is obtained by azeotropic distillation of a xylene/water mixture of the hydrated metal complex.

EXAMPLE 2

Preparation of ferric (III) acetylacetonate

To a solution composed of 12.1 grams (0.0745 mole) of ferric chloride (FeCl$_3$), 30 ml. of methanol and 26.8 grams (0.268 mole) of 2,4-pentenedione, about 25.9 grams (0.447 mole) of 1,2-propylene oxide were slowly added at ambient temperature and atmospheric pressure. Cold water was used to cool the reaction flask during the propylene oxide additions so as to maintain a temperature of below 50°C. The solution was intensely red during the propylene oxide additions which were completed within about 10 to 15 minutes. Ten minutes after the final addition of propylene oxide a considerable amount of ferric (III) acetylacetonate red crystals had formed. At this point the entire reaction mixture was transferred into 200 ml. of cold distilled water to precipitate any additional metal complex in the solution. The ferric (III) acetylacetonate red crystals were placed on a Buchner funnel and washed with small quantities of methanol to remove any residual trace of chlorohydrins. The metal complex product was air dried and then analyzed. The melting point of the ferric (III) acetylacetonate product without recrystallization was 181° C. (lit. 184°C.). The ferric (III) acetylacetonate red crystals weighed 23.8 grams which represents a yield of about 90.5 per cent.

| Product Analysis: | %Fe |
|---|---|
| Calcd.: | 15.8 |
| Found: | 15.8 |

EXAMPLE 3

Following the procedure of Example 2, copper (II) acetylacetonate was prepared using 2.69 grams (0.02 mole) of copper chloride (CuCl$_2$), 4.8 grams (0.048 mole) of 2,4-pentanedione; 4.64 grams (0.08 mole) of 1,2-propylene oxide and 10 ml. of methanol. The blue-violet copper (II) acetylacetonate complex product crystals were washed twice with 25 ml. of hexane. The air dried metal complex product weighed 4.4 grams which represents about an 84 per cent yield.

| Product Analysis: | %Cu |
|---|---|
| Calcd.: | 24.3 |
| Found: | 23.8 |

EXAMPLE 4

Following the procedure of Example 2, copper (II) bis(benzylacetone) was prepared using 1.34 grams (0.01 mole) of copper chloride (CuCl$_2$); 3.88 grams (0.024 mole) of benzoylacetonate; 2.32 grams (0.04 mole) of 1,2-propylene oxide and 10 ml. of methanol. The crude copper (II) bis(benzylacetone) complex crystal product was washed with 10 ml. of methanol and air dried and analyzed.

| Product Analysis: | %Cu |
|---|---|
| Calcd.: | 16.5 |
| Found: | 16.6 |

EXAMPLE 5

Following the procedure of Example 2, copper (II) bis(4,4,4-trifluoro-1-phenyl-1,3-butanedione) was prepared using 1.34 grams (0.01 mole) copper chloride (CuCl$_2$); 5.18 grams (0.024 mole) of 4,4,4-trifluoro-1-phenyl-1,3-butanedione; 2.32 grams (0.04 mole) of 1,2-propylene oxide and 10 ml. of methanol. The washed and air dried copper (II) bis (4,4,4-trifluoro-1-phenyl-1,3-butanedione) complex crystal product had a khaki color.

| Product Analysis: | %Cu |
|---|---|
| Calcd.: | 12.9 |
| Found: | 13.4 |

Various modifications and variations of this invention will be obvious to a worker skilled in the art and it is understood that such modifications and variations are to be included within the purview of this application and the spirit and scope of the appended claims.

What is claimed is:

1. A process for preparing metal complexes of organic 1,3-diketones having the general formula

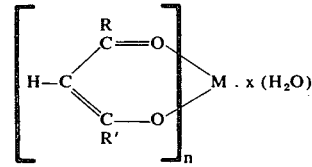

wherein R and R' are each individually monovalent organic radicals selected from the group consisting of alkyl, aryl, aralkyl, alkaryl, cycloalkyl, alkoxy, haloalkyl, and haloaryl radicals having from 1 to 12 carbon atoms; M is a metal cation selected from the group consisting of copper, zinc, mercury, lanthanum, cerium, praseodymium, neodymium, samarium, zirconium, chromium, uranium, manganese, iron, cobalt, nickel, platinum, palladium, cadmium, scandium, thorium, vanadium, ytturium, europium, gadolinium, hafnium, and plutonium, $n$ is an integer which corresponds to the electrovalence of M and $x$ has a value of O or a positive integer, which comprises reacting in the presence of an alkylene oxide and an inert organic polar solvent, a metal halide having the formula $M(X)_n \cdot y(H_2O)$ wherein M and $n$ are the same as defined above, X is halogen and $y$ has a value of O or a positive integer, and an organic 1,3-diketone having the formula $RCOCH_2COR'$ wherein R and R' are the same as defined above.

2. A process as defined in claim 1 wherein the metal halide employed is an anhydrous metal halide and $y$ has a value of O.

3. A process as defined in claim 1 wherein the metal halide employed is a hydrated metal halide and $y$ is a positive integer.

4. A process as defined in claim 1 wherein the alkylene oxide is a lower alkylene oxide having 2 to 4 carbon atoms.

5. A process as defined in claim 4, wherein the solvent is methanol and wherein the reaction is conducted at a temperature of about 50°C. or below and under atmospheric pressure.

6. A process as defined in claim 5, wherein R and R' are both methyl radicals and the alkylene oxide is 1,2-propylene oxide.

7. A process as defined in claim 1, wherein the metal is selected from the group consisting of nickel (II), copper (II) and iron (III).

8. A process as defined in claim 6, wherein the metal halide is selected from the group consisting of $NiCl_2$, $NiCl_2 \cdot 6H_2O$, $CuCl_2$ and $FeCl_3$.

9. A process as defined in claim 1, wherein the metal halide is hydrated nickel dichloride.

10. A process as defined in claim 7, wherein R and R' are lower alkyl radicals, wherein the alkylene oxide contains from 2 to 4 carbon atoms and wherein the solvent is a lower alkyl alcohol.

11. A process as defined in claim 6 for preparing the complex product of nickel (II) acetylacetonate dihydrate employing $NiCl_2 \cdot 6H_2O$ as the metal halide.

12. A process as defined in claim 11 wherein the nickel dihydrate complex product is dehydrated.

* * * * *

UNITED STATES PATENT OFFICE
CERTIFICATE OF CORRECTION

Patent No. 3,946,057　　　　　　　　　　Dated　March 23, 1976

Inventor(s)　James Dale Reedy

It is certified that error appears in the above-identified patent and that said Letters Patent are hereby corrected as shown below:

Column 1, line 36, that part of the formula shown as "M.X." should read ---M.x---.

Column 5, line 14, "ro" should be ---to---.

Claim 1, column 7, line 3, "ytturium" should be --- yttrium ---.

$\mathcal{S}$igned and $\mathcal{S}$ealed this

First Day of March 1977

[SEAL]

Attest:

RUTH C. MASON  
*Attesting Officer*

C. MARSHALL DANN  
*Commissioner of Patents and Trademarks*